United States Patent
Micheyl et al.

(10) Patent No.: US 6,974,410 B2
(45) Date of Patent: Dec. 13, 2005

(54) AUDITORY SIGNAL GENERATOR FOR PEOPLE SUFFERING FROM TINNITUS

(75) Inventors: Christophe Micheyl, Ste Foy-les-Lyon (FR); Arnaud Norena, Lyons (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/466,660

(22) PCT Filed: Jan. 18, 2001

(86) PCT No.: PCT/FR01/00163

§ 371 (c)(1),
(2), (4) Date: Feb. 4, 2004

(87) PCT Pub. No.: WO02/058434

PCT Pub. Date: Jul. 25, 2002

(65) Prior Publication Data

US 2004/0127812 A1    Jul. 1, 2004

(51) Int. Cl.[7] .............................................. H04R 25/00
(52) U.S. Cl. ....................................................... 600/25
(58) Field of Search ................... 600/25; 181/126–137; 381/312–321

(56) References Cited

U.S. PATENT DOCUMENTS 4,222,393 A    9/1980   Hocks

FOREIGN PATENT DOCUMENTS

| DE | 297 06 812 U | 9/1997 |
|----|--------------|--------|
| WO | WO 97 23117 A | 6/1997 |

*Primary Examiner*—John P. Lacyk

(57) ABSTRACT

The invention concerns an auditory signal generator for reducing, or even eliminating tinnitus. The invention is characterised in that it comprises the following operational phases: a) measuring the absolute auditory thresholds; b) measuring the perceived frequency of tinnitus; c) calculating on the basis of the measurements obtained characteristics of an auditory signal adapted to a subject's particular case, so as to programme said generator enabling it to deliver, with appropriate means, said correcting signal.

6 Claims, 5 Drawing Sheets

AUDITORY SIGNAL GENERATOR FOR PEOPLE SUFFERING FROM TINNITUS

This application is a U.S. National Phase Application under 35 U.S.C. § 371, and Applicant hereby claims the benefit of priority of PCT/FR01/00163 filed Jan. 18, 2001.

BACKGROUND

The present invention relates to a process for programming a device for generating auditory signals intended to be heard by people suffering from tinnitus. It also relates to a device implementing such a process, of which the characteristics of the signals generated are adapted specifically to the audiological characteristics of an individual in order to promote the disappearance or alleviation of tinnitus in this individual.

By tinnitus is meant the perception of noises in the ear or in the head which do not correspond to any acoustic signal in the environment. The nature of these noises and the intensity with which they are manifested can vary according to the case. Generally, the nuisance caused by tinnitus can be considerable to the subject; it can become debilitating and lead to serious psychological disorders, in particular mood and sleep disturbances. Moreover, most people who suffer from tinnitus also have a more or less serious hearing loss.

In a standard fashion, a person suffering from tinnitus is offered different types of treatments, the actual effects of which are not always conclusive. Pharmacology represents the most common method of treatment, but none of the substances prescribed has any demonstrated beneficial effect, and certain of them even have negative effects, to the extent of aggravating the nuisance caused by the tinnitus.

There are also tinnitus-masking devices which are systems delivering a sound signal into a patient's ear, in order to render the tinnitus inaudible, either directly and immediately, by perceptual masking, or progressively, by virtue of a process of physiological habituation.

The tinnitus maskers proposed at present pose several problems:
- the signal-generation possibilities of these systems are very limited. In fact, in most cases, they do not make it possible to produce a single type of signal with very simple spectral characteristics, which considerably limits the possibilities of adaptation to the particular case of each patient.
- moreover, the existing maskers are generally presented in the form of hearing aids. This type of device puts off a number of tinnitus patients, especially the younger ones, who do not have sufficient hearing loss to need to wear a hearing aid, and do not wish to give the impression of suffering from a handicap.
- finally, the insufficient adaptability of these maskers to the particular case of each tinnitus sufferer makes them ineffective and even, in certain cases, aggravates the severity of the disorder.

SUMMARY

The present invention thus aims to overcome these drawbacks by proposing a process for programming a device generating auditory signals, the physical characteristics of which are adapted to the particular case of a tinnitus sufferer: listening to them over a long period should lead to its final or temporary disappearance, or at the very least alleviate the tinnitus and the nuisance associated with it.

To this end, the process for programming an auditory signal generator, which is a subject of the invention, with a view to alleviating, even eliminating tinnitus, is characterized in that the following operational phases are carried out:
 a) measurement of the absolute auditory thresholds,
 b) calculation, on the basis of the measurements obtained, of the characteristics, also referred to as spectral envelope, of an auditory signal adapted to a subject's particular case, in order to programme said generator allowing it to deliver said auditory signal, using appropriate means.

The invention also relates to an auditory signal generator allowing implementation of the process, comprising appropriate means allowing it to deliver a corrective signal, comprising a device for multiplication of the spectral envelope with the spectrum of a white noise and inverse Fourier transform, for the purposes of direct use or for the purposes of storage within a support.

Other characteristics and advantages of the present invention will appear from the following description, with reference to the attached drawings, which illustrate an embodiment thereof, without any limiting character. In the figures:

DETAILED DESCRIPTION

Figure 1:
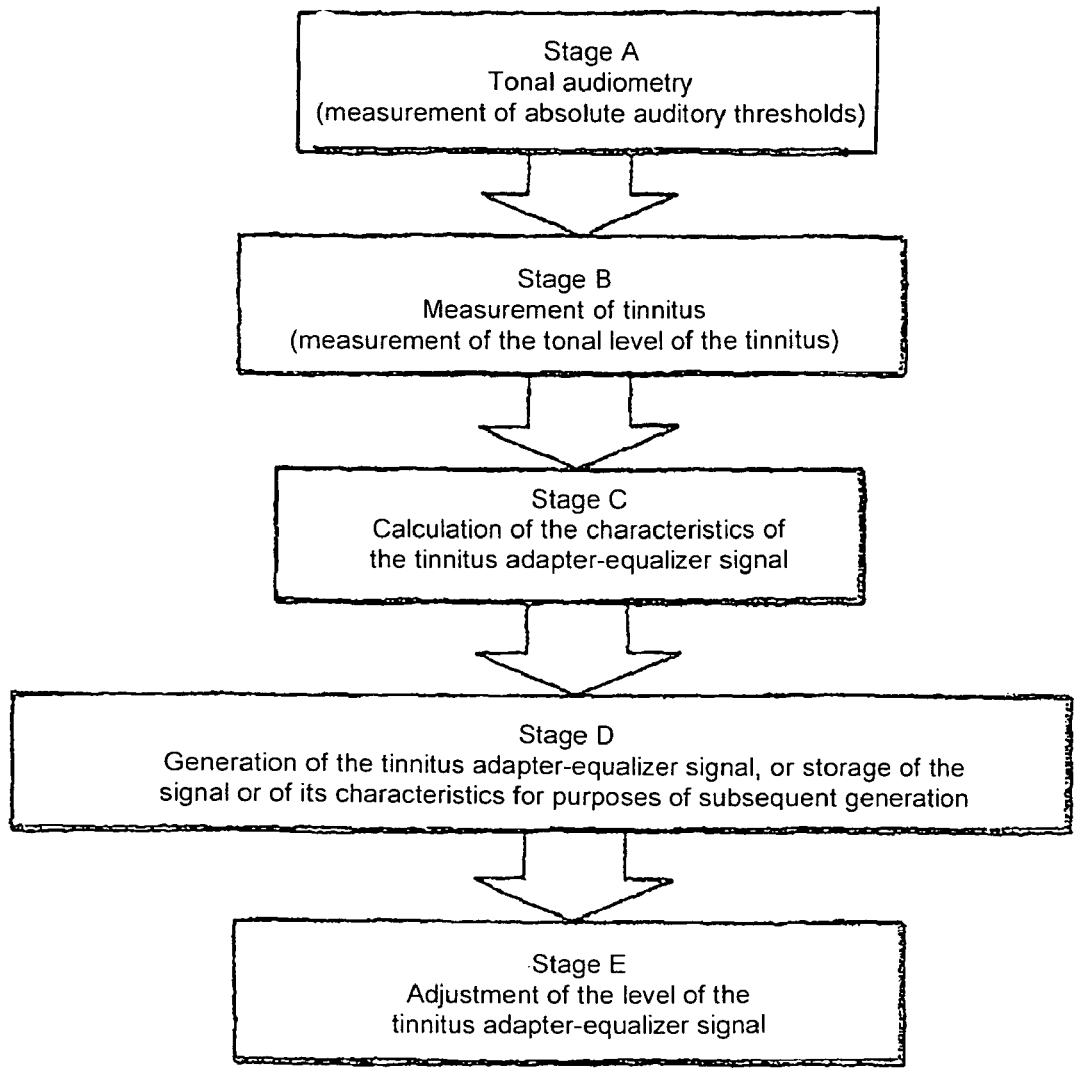
FIG. 1 represents the different stages of a process for programming an auditory signal generator, according to the invention.

According to a preferred method of implementation of the process according to the invention, said process for programming a sound-signal generator comprises 4 major distinct operational phases, and in particular an intermediate stage between the main stages a and b corresponding to the measurement of the perceived frequency of the tinnitus (FIG. 1):

In order to carry out the first stage and the intermediate stage, first and second means are used which can be identical. In particular, these first and second means can comprise a pure sound generator, logarithmic attenuators, a headphone preamplifier and a headphone.

A first operational phase (cf. stage a) consists of measuring the absolute auditory thresholds. These thresholds, defined as being the lowest intensity of sound that the subject can perceive, are measured using pure sounds of different frequencies, the intensity of which can be varied depending on the responses of the subject, who has the task of indicating, by means of a response device (of push button or other type), whether or not he can hear these sounds. In order to do this, an intermittent sound of given frequency and intensity is emitted by the first means into one of the subject's ears; the subject then indicates whether or not he has heard this sound. The sound emitted can be made up, for example, of three successive tonal bursts, each burst having a duration of 400 milliseconds, including advantageously raised cosine ramps of 20 milliseconds; the three bursts being separated by an interval of 200 ms. The frequency chosen can be 2000 Hz for example, and the level 60 decibels.

If the sound has been heard by the subject, the level of the signal is reduced by a certain quantity x in decibels (for example, 10 dB). On the other hand; if this same sound has not been heard, the level is increased by a quantity y in decibels (for example, 20 dB). The sound is then presented again, and the procedure is repeated, the quantities x and y being progressively reduced.

The criterion for stopping the procedure consists either of reaching a minimum level, or of carrying out a sufficient and prefixed number of inversions around the estimated threshold, or of reaching a prefixed minimum value.

When an estimate of this absolute auditory threshold at one given frequency is obtained, the measurement of the threshold at a subsequent frequency commences. This subsequent test frequency is determined by means of a device identical to the preceding one, and following a dichotomic procedure according to the following rules:

all the octave frequencies between 500 and 16,000 Hz (i.e. 500, 1000, 2000, 4000, 8000 and 16,000 Hz) are tested, in a pseudo-random order, in order to avoid the effects of habituation or fatigue.

if, at the end of these measurements, no relative increase in the threshold (i.e. a difference of more than 10 dB between the thresholds measured at one or other of the different frequencies tested) has been observed, threshold measurements are carried out at intermediate frequencies (one-half octaves), first about 4000 Hz, then at higher frequencies and at lower frequencies.

if a relative increase in threshold is observed by the subject at a given frequency, threshold measurements are carried out more precisely around this frequency, commencing by testing the higher and lower frequencies, according to a half-octave octave interval, then this frequency step is reduced and the measurement procedure resumes at the intermediate frequencies.

the criterion for stopping the procedure consists of reaching a minimum frequency step value or another criteria making it possible to attest that a sufficiently high level of precision has been reached. The absolute auditory thresholds are successively measured in both ears by means of the operational phase described above.

A second operational phase (cf. stage B) consists of measuring the perceived frequency of the tinnitus. This measurement of the level of the tinnitus is carried out either by means of a dichotomous framing procedure, or following an adjustment procedure. In the first case, an intermittent sound at a given frequency is emitted by the second means into at least one of the subject's ears. For example, this sound is made up of three 1-second pulses, each separated by 1 second of silence and at a frequency of 2000 Hz. The subject's task is to indicate by means of a response-box type interface whether this sound is higher or lower pitched than, or of the same tonality as, the tinnitus. The subject also has the possibility of hearing the same sound again before deciding.

If the sound emitted is higher pitched, the frequency of the test sound is divided by a certain factor. On the other hand, if this same sound is lower pitched, the frequency of the test sound is multiplied by the same factor. Then the procedure is repeated, the factor being reduced each time the subject's response is reversed (and increased each time the subject gives the same response more than twice in succession) until the value of this factor reaches a prefixed minimum value or the subject indicates that the test sound has the same tonality as the tinnitus.

According to an advantageous characteristic of the process according to the invention and by the effect of a generator implementing said process, the third means making it possible to adjust, at each frequency, the level of test sound on the basis of the results of the measurement of the thresholds produced in the first stage, so that this level is maintained between 5 and 10 dB above the absolute threshold and is thus always approximately at the same perceived intensity as the tinnitus. This adjustment has the advantage of considerably facilitating the measurement of the tonal level of the tinnitus. In fact, the intensity being a crucial factor for the characterization of the level of the tinnitus, by neutralizing the effect of the latter, it is easier to localize the frequency which corresponds to the level of the tinnitus.

After a first estimate of the tinnitus frequency has been obtained, other successive measurements are carried out, until a sufficient reproducibility criterion of the measurement has been reached. Such a criterion consists, for example, of obtaining a 95% confidence interval having a range equal to or less than a required and predefined minimum range around the estimated tonal level of the tinnitus.

In subjects who indicate that they perceive their tinnitus in one ear, the measurement of the level of the tinnitus according to the operational phase described above is carried out successively with said intermittent sound presented in this ear (ipsilateral matching), then in the opposite ear (contralateral matching). In subjects who indicate that they perceive tinnitus centred in the intracranial space, the matching sound is presented simultaneously in both ears, with the same phase. In subjects who say that they perceive tinnitus localized in both ears, the matching of the tinnitus of each ear is carried out by presenting the test sound in the same ear (ipsilateral matching).

At the end of this stage of tinnitus tonal level measurement, it is verified that this level falls into, or close to a frequency zone in which the absolute auditory thresholds are increased.

The third operational phase (cf. Stage C) consists of determining, on the basis of the measurements obtained, the characteristics of an adapter-equalizer signal adapted to the particular case of the subject.

Thus, starting with the data measured in the preceding stages, the spectral envelope still referred to as characteristic of the signal is calculated using algorithms in order to compensate for the hearing loss or losses measured in the first stage. Diagrammatically, this envelope corresponds to the negative (on the scale of ordinates representing a gain in intensity) of the tonal audiogram measured in the first stage: the amplitude of this envelope is greater in the regions in which the absolute auditory thresholds are highest.

Figure 2:
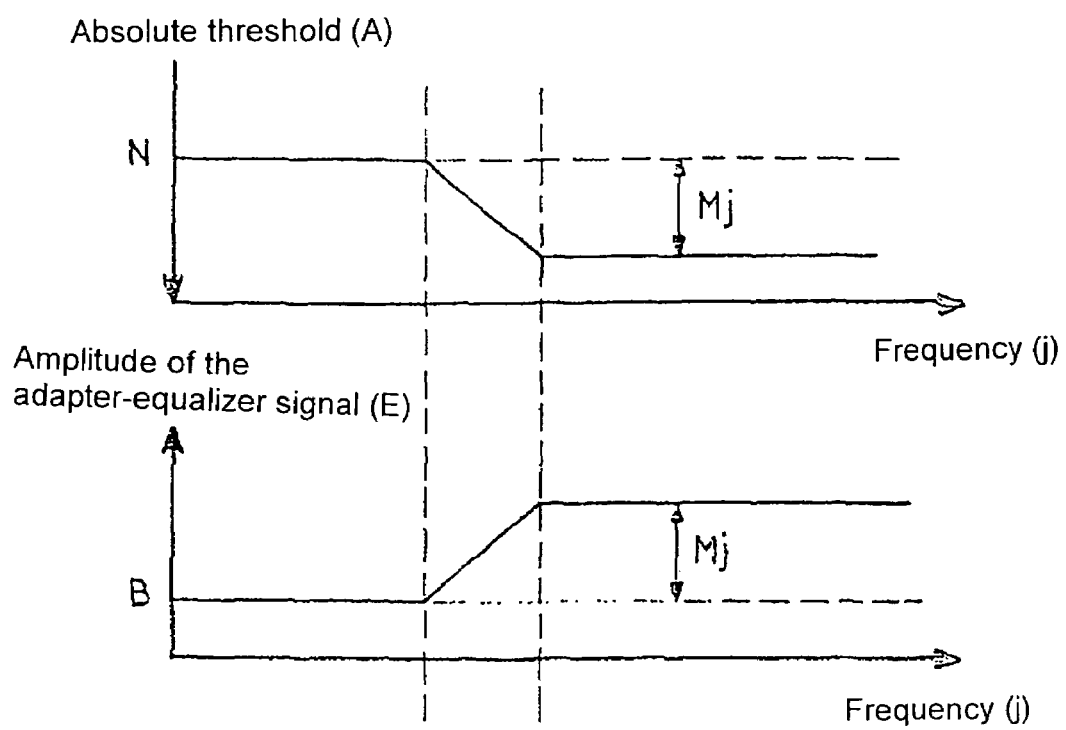
FIG. 2 diagrammatically represents the calculated form of the spectral envelope of the adapter-equalizer signal according to the invention.

The algorithmic formulae for the calculation of this envelope of the adapter-equalizer signal starting from the tonal audiogram are as follows:

Let $A_i$ be the absolute auditory thresholds (in decibels) at the different frequencies $F_i$ at which these thresholds have been tested, let $A_j$ be the absolute auditory thresholds at the frequencies $F_j$ (estimated by interpolation from the $A_i$'s measured) with j belonging to the group of integers [1; N] where N is the number of points in the spectral window, and let $F_j = j*(F_e/N)$, $F_e$ being the sampling frequency. The spectral envelope of the adapter-equalizer signal at each point j of the spectral window is then calculated using the following mathematical formula:

$$Ej = B + Mj - Qr(Aj)$$

where: B represents the minimum level of the adapter-equalizer signal; $Mj = N - Aj$ where N is the average of the minimum thresholds obtained with the tonal audiometry; and $Qr(Aj)$ is a correction factor introduced to take account of the effects of the cochlear compression and reduction of frequency selectivity over the quantity of excitation produced by the signal in the auditory system. FIG. 2 diagrammatically represents the spectral envelope of the adapter-equalizer signal thus calculated from the absolute auditory thresholds.

Figure 3:
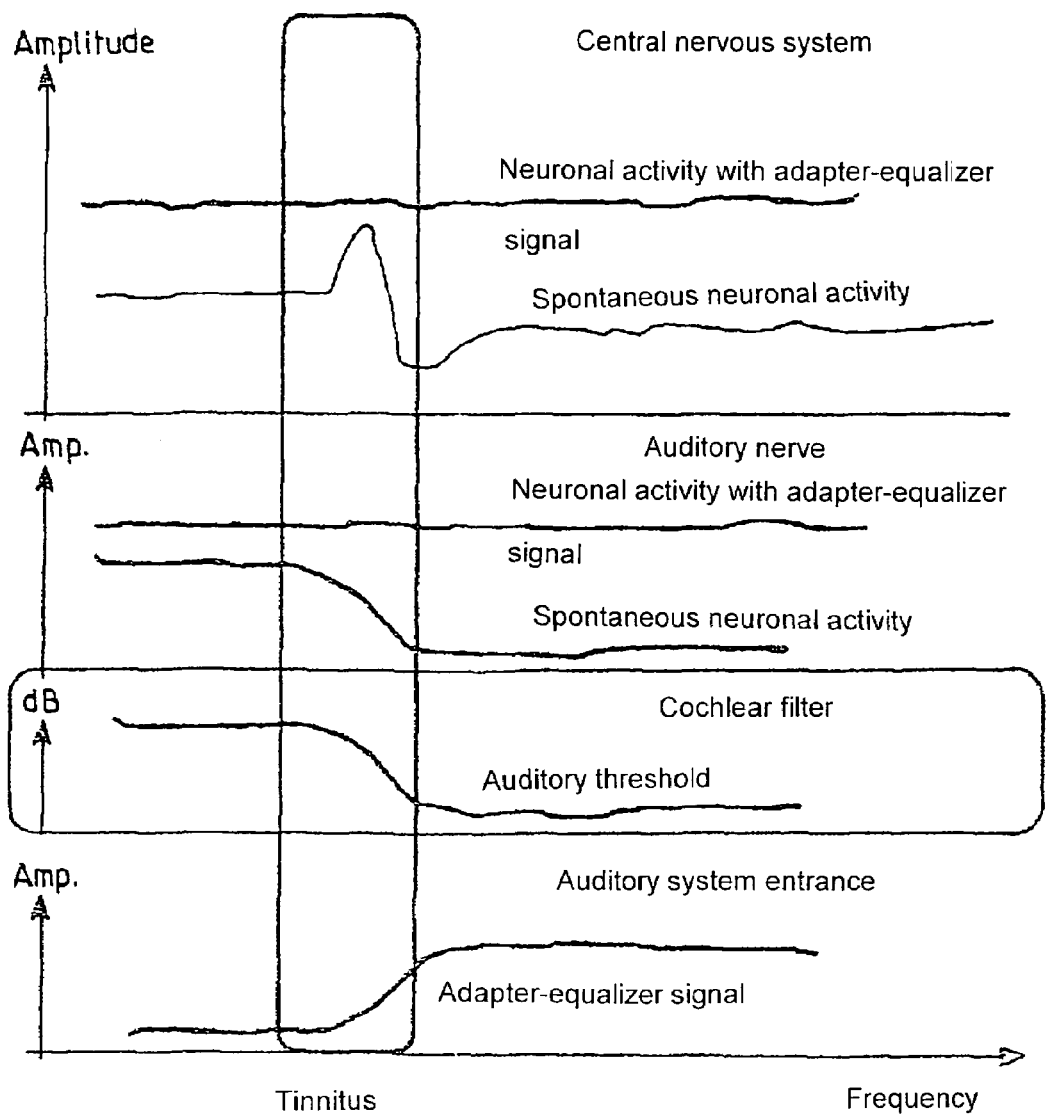
FIG. 3 is a representation on several levels of the auditory system of the neuronal responses caused by an adapter-equalizer signal.
Figure 4:
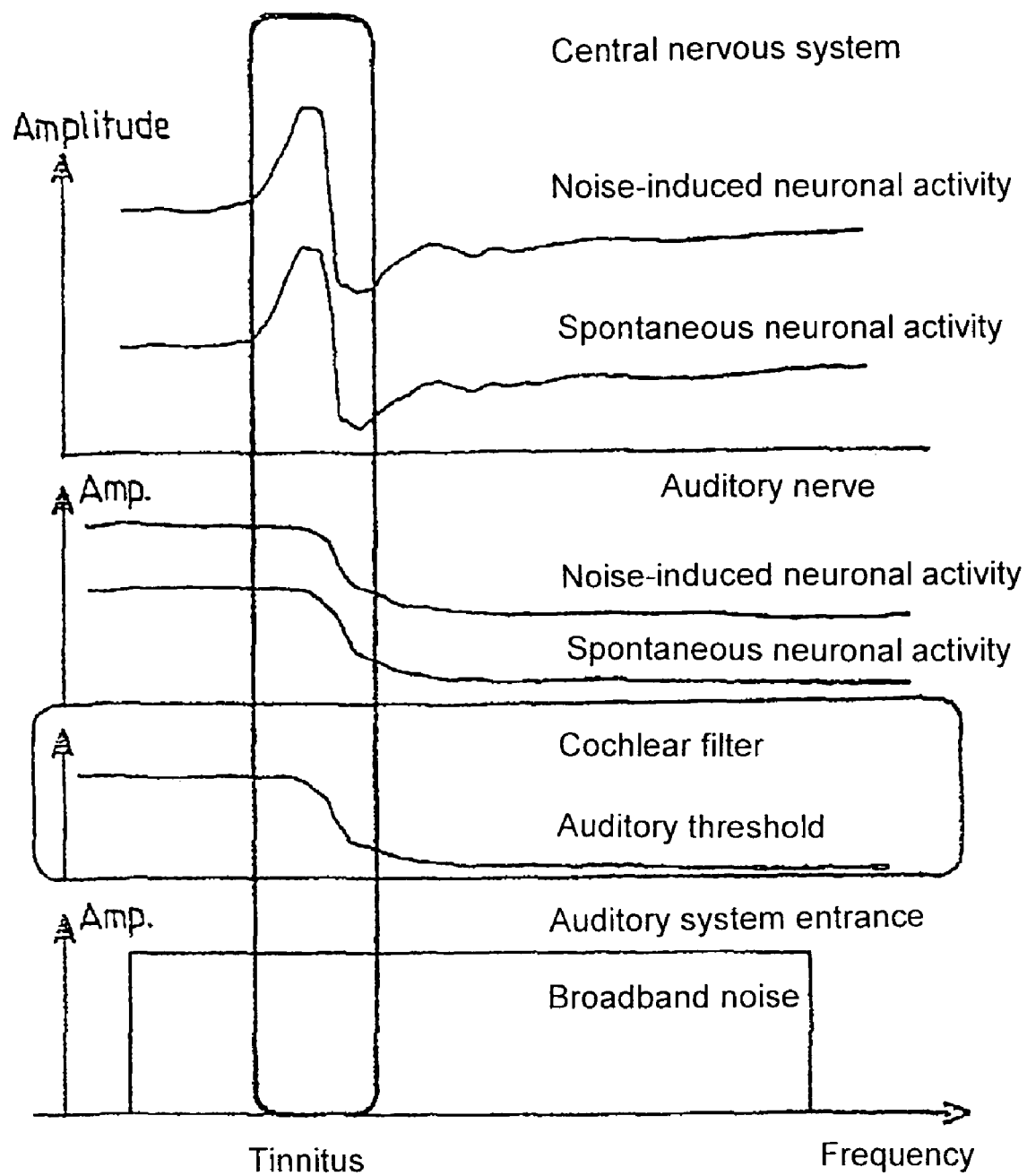
FIG. 4 is a representation on several levels of the auditory system of the neuronal responses caused by a white noise.

Thus, and according to an advantageous characteristic of the process according to the invention, the characteristics of said auditory signal as exactly as possible compensate for the subject's hearing loss, in order to eliminate the spectral contrasts in the activity of the auditory system which are caused by the hearing loss. In other words, this signal is intended to make the discontinuities in the activity of the neurons across the frequencies disappear. FIG. 3 represents, at several levels of the auditory system, neuronal responses evoked by such an adapter-equalizer signal in the presence of a hearing loss. By comparison, FIG. 4 represents the same diagram of neuronal responses evoked by a white noise used in the tinnitus-masking devices currently available on the market: with an adapter-equalizer signal calculated and programmed according to the invention and adapted to the particular case of each subject, this is approximately level and constant, whereas with a white-noise-type signal, the neuronal activity always presents a peak at the level of the tinnitus frequency, which is interpreted as a sound by the central nervous system.

A characteristic of the present invention with respect to these devices (as well as those which, more generally, deliver a signal whose characteristics are not adapted to the individual's hearing loss) is that the characteristics of the signal are determined on the basis of a previous measurement of the precise form of the subject's hearing loss.

Figure 5:
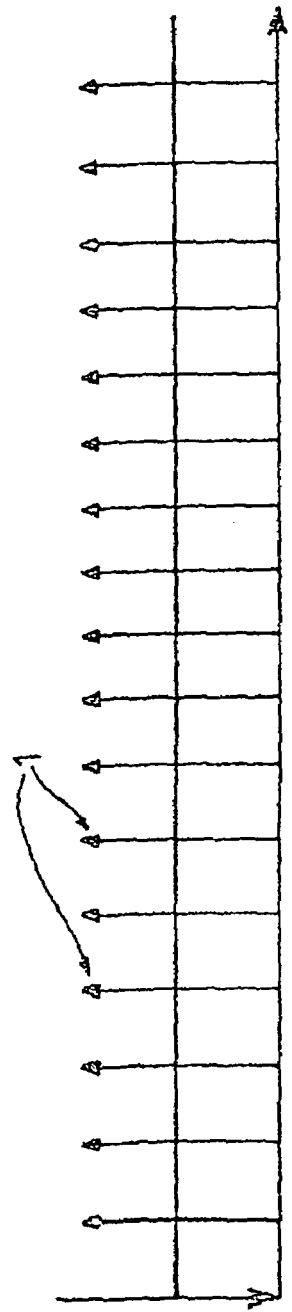
FIGS. 5a, 5b and 5c represent the tonotopic organization of the central neurons in, respectively, a subject with normal hearing, a subject with tinnitus with hearing loss, and the same subject after listening to an adapter-equalizer signal.
Figure 5:
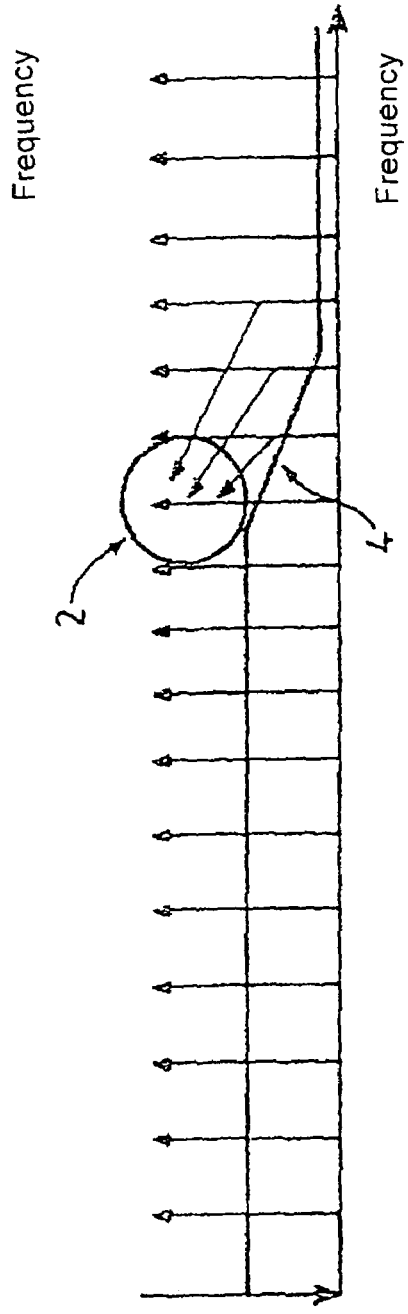
Figure 5:
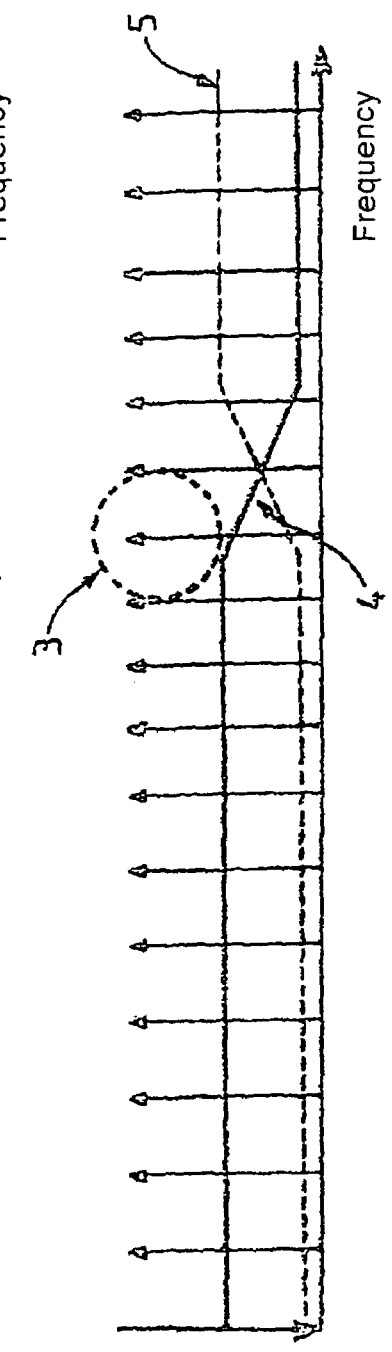

Moreover, only such a signal specifically adapted to the hearing of the subjects, subjected for a long enough period to the auditory system, leads, within the latter, to a reversal of the cerebral plasticity mechanisms following the appearance of the hearing loss, and associated with the emergence and persistence of tinnitus. Thus, FIGS. 5a to 5c represent the tonotopic organization of the central neurons in a subject with normal hearing (FIG. 5a), in a subject with tinnitus with hearing loss (FIG. 5b) and in the same subject with tinnitus after listening to the adapter-equalizer signal for a sufficient period of time (FIG. 5c). In these figures, the reference points 1 represent the neurons organized in tonotopic fashion (at a given position, a reduced frequency band corresponds). In FIG. 5b, the neurons corresponding to the hearing loss boundary 4 correspond to the adjacent frequencies: a frequency zone 2 is therefore found "over-represented" at the central level (this zone corresponds to the frequency of the tinnitus). As represented in FIG. 5c, the adapter-equalizer signal 5 then reverses the plasticity mechanisms induced by the hearing loss (normalization of the central tonotopic organization, reference point 3).

The fourth operational phase of the process according to the invention and, incidentally, a characteristic of a generator allowing the implementation of said process (cf. stage D) consists of the generation of the auditory signal or the fixation of this signal or of its characteristics on a storage support for purposes of subsequent restitution. In fact, once the characteristics of the adapter-equalizer signal have been calculated, this signal can, depending on the user's choice, be generated directly in its temporal form (by multiplication of the spectral envelope with the spectrum of a white noise, then inverse Fourier transform) for the purposes of direct use (for example by electroacoustic transduction) or for the purposes of storage within a digital- or analogue-type support, chosen for example from compact discs, mini-discs, cassettes, hard discs, or floppy disks, this use or this storage being obtained by appropriate means.

The characteristics of the signal can also be used to programme an electronic device included in these means (for example, a programmable memory containing coefficients characteristic of the transfer function of a numeric filter, said coefficients can be calculated in particular by Z transformation) intended to participate in the restitution of the signal by a device (for example a hearing aid or a device for generating acoustic signals fitted around the ear, or an intra-auricular device).

According to an advantageous characteristic of the invention, the process according to the invention comprises a final operational phase (cf. Stage E) which consists of adjusting, by interaction with the subject, the intensity of the adapter-equalizer signal also called corrective signal. The latter must not totally mask the tinnitus and must be of a sufficient intensity to optimize its effectiveness.

The minimum level of tinnitus maskability is automatically sought using an ascending procedure by virtue of which the level of the signal is progressively increased in order to avoid the phenomenon of residual inhibition. Once the masking threshold is obtained, the signal level is advantageously adjusted between 5 and 10 dB below it.

The present invention as described previously, offers a number of advantages; in particular, it makes it possible to specifically adapt the signal to the hearing loss of each patient suffering from tinnitus. The useful components of the signal (those located in the subject's hearing loss zone) being amplified with respect to those which fall outside the loss, the stimulation level can be lower than that used with the devices which generate signals which are not as precisely adapted to the subjects' hearing. This property confers greater listening comfort on the adapter-equalizer signal. In fact, the lower the signal level, the less the individuals are disturbed in their daily activities. Moreover, the flexibility provided by the possibility of storing the signal on any support that the patients can listen to by means of a Walkman or audio system at home or outside, provides considerable comfort in use to these patients who are generally used to more restrictive approaches.

Of course the present invention is not limited to the examples of implementation and embodiments described above, but it includes all variants thereof.

What is claimed is:

1. Process for programming an auditory signal generator for treating tinnitus comprising:

measuring absolute auditory thresholds of a subject, and calculating on the basis of the measuring step characteristics of an auditory signal adapted to the subject's auditory threshold using substantially the following equation:

$$Ej = B + Mj - Qr(Aj)$$

where B is a minimum level of said auditory signal; $Mj = N - Aj$ with N being an average of minimum thresholds obtained and Aj are absolute auditory thresholds, and $Qr(Aj)$ is a correction factor; and programming said auditory signal generator to produce a corrective signal based on the calculated characteristics, to treat tinnitus.

2. Process according to claim 1 further comprising measuring perceived frequency of the tinnitus of the subject.

3. Process according to claim 1 wherein the measuring step further comprises:
- emitting into the right or left ear of the subject an intermittent sound having intensity and frequency, and
- varying the intensity and frequency depending on the responses given by said subject using a response device, said subject having the task of indicating whether he has heard said intermittent sound.

4. Process according to claim 1 wherein measuring the perceived frequency of the tinnitus further comprises:
- emitting into one of the right and left ear of the subject an intermittent sound, and
- varying the frequency of the intermittent sound depending on the responses given by said subject using a response device, said subject having the task of indicating whether said intermittent sound is higher pitched, lower pitched or of the same tonality as the tinnitus.

5. Process according to claim 1 further comprising adjusting the intensity of said auditory signal so as to optimize its effectiveness.

6. Process according to claim 1 wherein characteristics of said auditory signal are such that they compensate as exactly as possible for a hearing loss.

* * * * *